United States Patent

Jacks et al.

Patent Number: 5,998,633
Date of Patent: Dec. 7, 1999

[54] PROCESS FOR THE SYNTHESIS OF PROTECTED ESTERS OF (S)-3,4-DIHYDROXYBUTYRIC ACID

[75] Inventors: Thomas E. Jacks; Donald E. Butler, both of Holland, Mich.

[73] Assignee: Warner-Lambert Company, Morris Plains, N.J.

[21] Appl. No.: 09/230,397

[22] PCT Filed: Jul. 1, 1997

[86] PCT No.: PCT/US97/11654

§ 371 Date: Jan. 27, 1999

§ 102(e) Date: Jan. 27, 1999

[87] PCT Pub. No.: WO98/04543

PCT Pub. Date: Feb. 5, 1998

Related U.S. Application Data

[60] Provisional application No. 60/022,369, Jul. 29, 1996.

[51] Int. Cl.$^6$ .................... C07C 59/10; C07C 69/675; C07D 307/20; C07D 317/12
[52] U.S. Cl. ............................. 549/313; 549/454
[58] Field of Search .................... 549/313, 454; 560/189; 562/579

[56] References Cited

U.S. PATENT DOCUMENTS 5,292,939  3/1994  Hollingsworth .

FOREIGN PATENT DOCUMENTS 0513430  11/1992  European Pat. Off. .
9804543   2/1998   WIPO .

OTHER PUBLICATIONS

Ahn et al., Tetrahedron Let. 33(4), 507–510, 1992.
Reese, Protective Groups in Org. Chem. p. 120–143, 1973.
Lee et al., J. Org. Chem. (1993) 58, 1887–94.
Tokunaga et al., J. Chem. Soc., Perkin Trans. 1 (1986) 581–4.
Lag Cheveque et al. Tetrahedron, 43(10), 2303–10, 1987.
Saito et al., Tetrahedron, 48(20), 4067–86, 1992.

Primary Examiner—Joseph K. McKane
Assistant Examiner—Taofiq A. Solola
Attorney, Agent, or Firm—Francis J. Tinney

[57] ABSTRACT

The invention is an improved process for the preparation of a compound of formula I wherein R and $R^1$ are each independently alkyl of from 1 to 3 carbon atoms; and $R^2$ is alkyl of from 1 to 8 carbon atoms.

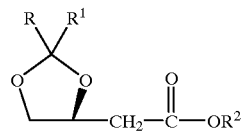

I

39 Claims, No Drawings

PROCESS FOR THE SYNTHESIS OF PROTECTED ESTERS OF (S)-3,4-DIHYDROXYBUTYRIC ACID

This application claim the benefit of Provisional Appln. No. 60/022,369 filed Jul. 29, 1996.

BACKGROUND OF THE INVENTION (S)-3-Hydroxybutyrolactone and a derivative, methyl (S)-3,4-O-isopropylidene-3,4-dihydroxybutanoate, are optically active starting materials in the preparation of [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) (atorvastatin), a new HMG-CoA reductase inhibitor (Nanninga, et al., *Tetrahedron Lett.*, 1992;33:2279).

Chiral dihydroxybutyric acids and the corresponding esters, lactones, and derivatives have proven to be valuable chemical entities. In addition to useful intermediates in synthetic efforts towards natural products (Cf Benezra, et al., *J. Org. Chem.*, 1985;50:1144; Hanessian, et al., *Can. J. Chem.*, 1987;65:195; Ahn, et al., *Tetrahedron Lett.*, 1992:507), a number of clinical applications have been disclosed. (S)-3-Hydroxybutyrolactone has been reported as a satiety agent (Okukado, et al., *Bull. Chem. Soc. Jpn.*, 1988;61:2025) as well as a potentiating agent to neuroleptic drugs (Fuxe, et al., U.S. Pat. No. 4,138,484).

Clearly, there is a need for a simple and inexpensive method for the large scale preparation of (S)-3,4-dihydroxybutyric acid, (S)-3-hydroxybutyro-lactone, and derivatives of these chiral molecules. A large number of small scale complex syntheses have been reported demonstrating the value of these compounds.

Preparation of methyl (S)-3,4-O-isopropylidene-3,4-dihydroxybutanoate has been reported in the literature. It is prepared by reduction of dimethyl malate with borane-dimethyl sulfide complex/NaBH$_4$ followed by acid catalyzed reaction with dimethoxypropane to yield the acetonide (Saito, et al., *Chem. lett.*, 1984:1389; *Tetrahedron*, 1992;48:4067).

The acetonide has been prepared from isoascorbic acid via a multi-step sequence, but the yield was quite low due to the instability of an intermediate in the synthetic strategy (Tanaka, et al., *Synthesis*, 1987:570). The ethyl ester of the acetonide can be prepared from D-isoascorbic acid (Abushanab, et al., *Synth. Comm.*, 1989;19:3077) via a similar multi-step route. An enzymatic resolution starting with racemic dimethyl malate has also been employed to produce the acetonide methyl ester on a small scale (Benezra, et al., *J. Org. Chem.*, 1985;50:1144).

An additional reported procedure (Williams, et al., *Tetrahedron Lett.*, 1988;29:5087) involves the direct oxidation of the corresponding acetonide aldehyde with alcoholic bromine to give the acetonide methyl ester in good yield.

Although there are a variety of routes to this acetonide ester, they all involve either expensive starting materials, difficult to handle reagents, or multi-step sequences.

There are a number of procedures in the literature for the preparation of (S)-3,4-dihydroxybutyric acid and the corresponding internal ester, (S)-3-hydroxybutyrolactone. The oxidation of water soluble carbohydrates to (S)-3,4-dihydroxybutyric acid and the corresponding lactone, (S)-3-hydroxybutyrolactone, has been reported (Hollingsworth, U.S. Pat. Nos. 5,292,939; 5,319,110; and 5,374,773). However, there is no discussion on how to isolate the product, (S)-3-hydroxybutyrolactone, except by chromatography. This hydroxylactone is very difficult to isolate from the reaction mixture due to the high water solubility of the molecule and the ease of decomposition/dehydration at the high temperatures required for purification by distillation. The preparation discussed in these patents is performed at high dilution, presumably due to the highly exothermic nature of the oxidation. In addition, this preparation does not provide the hydroxylactone ((S)-3-hydroxybutyrolactone) in the yields reported. Thus, this process is not readily amenable to large scale, economical preparations of (S)-3-hydroxybutyrolactone. Further, the above patents do not discuss the preparation of esters of (S)-3,4-O-isopropylidene-3,4-dihydroxybutyrate directly from carbohydrate oxidation reaction mixtures.

Preparation of (S)-3-hydroxybutyrolactone has been reported in a multi-step procedure starting with (S)-malic acid (Prestwich, et al., *J. Org. Chem.*, 1981;46:4319). A slightly shorter route from either (S)-malic acid or aspartic acid has been reported (Larcheveque, et al., *Synth. Commun.*, 1986;16:183) although the optical conversion of aspartic acid to malic acid was not 100% due to racemization of an intermediate. Esters of (S)-malic acid have also been utilized (Saito, et al., *Chem. Lett.*, 1984:1389) using borane-dimethyl sulfide/sodium borohydride to prepare the dihydroxy ester followed by acid catalyzed cyclization to (S)-3-hydroxybutyrolactone.

A six-step procedure from D-isoascorbic acid has been reported (Tanaka, et al., *Synthesis*, 1987:570) but requires a diastereomeric separation and has been performed only on a small scale with purification by silica gel chromatography.

Oxidation and acid catalyzed cyclization of 6-(2,3-dihydroxypropyl)-1,3-dioxin-4-one has provided (s)-3-hydroxybutyrolactone in high optical purity but entails a six-step procedure (Sakaki, et al.; *J. Chem. Soc., Chem. Commun.*, 1991:434).

Rabbit muscle aldolase catalyzed condensation of 3-hydroxy-4-oxobutanoate with dihydroxy acetone phosphate (DHAP) provided (S)-3-hydroxybutyrolactone with excellent optical purity on small scale (Whitesides, et al., *J. Org. Chem.*, 1993;58:1887).

The preparation of (S)-3,4-dihydroxybutyric acid from (R)-3-chloro-1,2-propanediol via cyanation and hydrolysis of the dihydroxynitrile has been reported (Inoue, et al., U.S. Pat. No. 4,994,597). Oxidation of the corresponding hydroxyketone with perhexahydrobenzoic acid provides the 3-hydroxybutyrolactone (Cotarca, et al., International Published Patent Application, WO 94/29294) but no report of chiral purity is made.

The opposite enantiomer has been prepared by yeast reduction and cyclization of the appropriate ketoester (Seebach, et al., *Synthesis*, 1986:37). L-ascorbic acid (Luk, et al., *Synthesis*, 1988:226; Tanaka, et al., *Synthesis*, 1987:570) has been utilized to synthesis (R)-3-hydroxybutyrolactone via multi-step processes.

Optical resolution of racemic hydroxylactones using lipase has been reported (Miyazawa, et al., U.S. Pat. No. 5,084,392) but suffers due to only moderate enantiomeric excess and loss of the opposite enantiomer. Long reaction times are also reported with this procedure. Carbonylation of glycidol using a cobalt catalyst has been employed but requires high pressures to effect carbonylation and produces a significant quantity of unsaturated ester. The use of a chiral glycidol in the process to provide optically active lactones is not addressed (Brima, et al., U.S. Pat. No. 4,968,817). Acid catalyzed deprotection and subsequent lactonization of methyl (R)-3,4-O-isopropylidene-3,4-dihydroxybutanoate has been employed to prepare (R)-3-hydroxybutyrolactone (Luk, et al., *Synthesis*, 1988:226; Tanaka, et al., *Synthesis*, 1987:570). The corresponding cyclohexylidene protected ester of methyl (S)-3,4-dihydroxybutyrate has been deprotected and lactonized with dilute aqueous acid to provide (S)-3-hydroxybutyrolactone (Tanaka, et al., *Synthesis*, 1987:570).

Direct formation of the acetonide methyl ester from a similar hydroxylactone has been reported in the literature, but this procedure employs a purified lactone as the starting material (Larcheveque, et al., *Tetrahedron*, 1987;43:2303).

The object of the present invention is an inexpensive, scalable, direct route to esters of (S)-3,4-O-isopropylidene-3,4-dihydroxybutyric acid and (S)-3-hydroxybutyrolactone from a carbohydrate source.

SUMMARY OF THE INVENTION

Accordingly, a first aspect of the present invention is an improved process for the preparation of a compound of Formula I

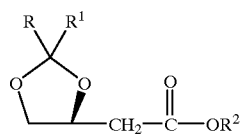

I wherein R and $R_1$ are each independently alkyl of from 1 to 3 carbon atoms; and $R^2$ is alkyl of from 1 to 8 carbon atoms, which comprises:

Step (a) treating a carbohydrate substrate in a solvent with hydrogen peroxide in the presence of a base and subsequent acidification with an acid to afford a mixture comprising a compound of Formula IV

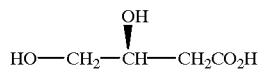

IV and glycolic acid;

Step (b) removing the solvent to convert the compound of Formula IV to the compound of Formula II

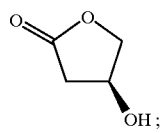

II

Step (c) treating the mixture containing the compound of Formula II with an alcohol of Formula VI $R^2$—OH      VI wherein $R^2$ is as defined above in the presence of an acid catalyst to afford a compound of Formula V

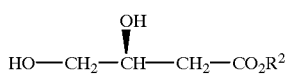

V wherein $R^2$ is as defined above; and

Step (d) treating the mixture containing a compound of Formula V with a compound of Formula III

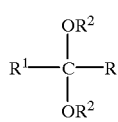

III wherein R, $R^1$, and $R^2$ are as defined above in the presence of an acid catalyst to afford a compound of Formula I.

A second aspect of the present invention is a process for the preparation of a compound of Formula Ia

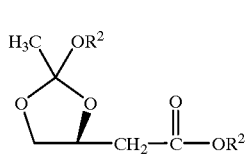

Ia wherein $R^2$ is alkyl of from 1 to 8 carbon atoms, which comprises:

Step (a) treating a carbohydrate substrate in a solvent with hydrogen peroxide in the presence of a base and subsequent acidification with an acid to afford a mixture comprising the compound of Formula IV

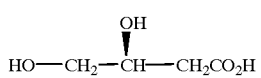

IV and glycolic acid;

Step (b) removing the solvent to convert the compound of Formula IV to the compound of Formula II

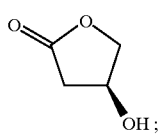

II

Step (c) treating the mixture containing the compound of Formula II with an alcohol of Formula VI $R^2$—OH      VI wherein $R^2$ is as defined above in the presence of an acid catalyst to afford a compound of Formula V

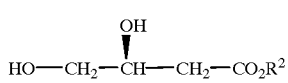

V wherein $R^2$ is as defined above; and

Step (d) treating the mixture containing a compound of Formula V with a compound of Formula IIIa

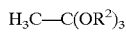

wherein R² is as defined above in the presence of an acid catalyst to afford a compound of Formula Ia.

DETAILED DESCRIPTION OF THE INVENTION

In this invention, the term "alkyl" means a straight or branched hydrocarbon group having from 1 to 8 carbon atoms and includes, for example, methyl, ethyl, n-propyl, isopropyl, n-butyl, isobutyl, tertiary-butyl, n-pentyl, tertiary-amyl, n-hexyl, n-heptyl, n-octyl, and the like.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

The process of the present invention is a new, improved, economical, and commercially feasible method for preparing a compound of Formula I and Formula Ia. The process of the present invention in its first aspect is outlined in Scheme I.

The compound of Formula IV is prepared from a carbohydrate substrate such as, for example, a water soluble carbohydrate, a disaccharide or greater oligomer, for example lactose, maltose, maltodextrins, and the like by oxidization with hydrogen peroxide in the presence of a base such as, for example, an alkali metal hydroxide, for example sodium hydroxide, potassium hydroxide, and the like, an alkaline earth metal hydroxide, for example calcium hydroxide and the like in a solvent such as, for example, water and the like at about 25° C. to about 80° C. for about 2 to about 24 hours followed by acidification of the reaction mixture with an acid such as, for example, hydrochloric acid, hydrobromic acid, and the like to a pH of about 0 to about 3 to afford a mixture containing the compound of Formula IV, glycolic acid and organic by-products. Preferably, the reaction is carried out with lactose and hydrogen peroxide in water in the presence of sodium hydroxide at about 65° C. to 75° C. for about 4 to about 10 hours followed by acidification with 37% hydrochloric acid solution to a pH less than 1.5.

The solvent is removed, for example, by distillation at a temperature of about 35° C. to about 75° C. under vacuum to convert the compound of Formula IV to the lactone of Formula II. Preferably, the solvent is removed by distillation under vacuum at a temperature of up to about 65° C.

The mixture containing the compound of Formula II is taken up in an alcohol of Formula VI wherein R² is alkyl of from 1 to 8 carbon atoms such as, for example, methanol, ethanol, and the like, and the by-product salts are removed by filtration. Preferably, the compound of Formula II is taken up in methanol. An acid catalyst such as, for example, hydrochloric acid, sulfuric acid, para-toluenesulfonic acid, and the like is added to the previous alcohol mixture, and the mixture is reacted at about room temperature to about the reflux temperature of the solvent for about 5 minutes to about 3 hours. Preferably, the acid catalyst is hydrochloric acid, and the mixture is reacted at reflux for about 2 hours. The volatiles are removed, for example, by distillation at about atmospheric pressure to distillation under vacuum at about 75° C. until no further by-product glycolate ester distills. Preferably, the solvent is removed by distillation at atmospheric pressure, followed by distillation under vacuum at a temperature of about 75° C. To the reaction mixture containing the compound of Formula II is charged an alcohol having from 1 to 8 carbon atoms such as, for example, methanol, ethanol, 2-propanol, n-butanol, and the like and an acid catalyst such as, for example, a mineral acid, for example, hydrochloric acid and the like, an organic acid, for example, para-toluenesulfonic acid and the like and the mixture reacted at about room temperature to the reflux temperature of the solvent for about 30 minutes to about 8 hours to afford a compound of Formula V, which is not isolated but reacted with a compound of Formula III wherein R and R¹ are each independently alkyl of from 1 to 3 carbon atoms and R² is alkyl of from 1 to 8 carbon atoms, for example, dimethoxypropane, diethoxypropane and the like and the mixture reacted at about room temperature to the reflux temperature of the solvent for about 30 minutes to about 8 hours and subsequent removal of the solvent, for example, by distillation to afford a compound of Formula I. The compound of Formula I is isolated from the crude reaction mixture by distillation under vacuum. Preferably, the reaction is carried out in methanol and dimethoxypropane in the presence of paratoluenesulfonic acid for about 1 hour with subsequent removal of the solvent by distillation. After removal of the excess solvent, a compound of Formula I is isolated from the crude reaction mixture by distillation under vacuum.

The process of the present invention in its second aspect is outlined in Scheme II.

In an analogous manner using the methodology used to prepare a compound of Formula I, a compound of Formula Ia wherein R² is as defined above is prepared from a carbohydrate substrate. Thus, the compound of Formula V is treated with an orthoester of Formula IIIa wherein R² is as defined above such as, for example, trimethyl orthoacetate, triethyl orthoacetate, and the like to afford a compound of Formula Ia.

Compounds of Formula III and Formula IIIa are either known or may be prepared by methods known in the art.

(S)-3-Hydroxybutyrolactone and methyl (S)-3,4-O-isopropylidene-3,4-dihydroxybutanoate (as described previously) can be employed as starting materials in the preparation of ethyl (S)-4-bromo-3-hydroxybutanoate by treatment with HBr in acetic acid followed by esterification with ethanol (Taoka, et al., Japanese patent application JP 90-271608, filed Oct. 9, 1990) or by treatment with trimethylsilyl bromide and ethanol (Larcheveque, et al., *Tetrahedron*, 1990;46:4277).

Nanninga T., et al., *Tetrahedron Letters*, 1992;33:2279 disclose the use of ethyl (S)-4-bromo-3-hydroxybutanoate in the preparation of ethyl (R)-4-cyano-3-hydroxybutanoate which is employed in the preparation of [R-(R*,R*)]-2-(4-fluorophenyl)-β,δ-dihydroxy-5-(1-methylethyl)-3-phenyl-4-phenylaminocarbonyl-1H-pyrrole-1-heptanoic acid, calcium salt (2:1) (atorvastatin) which is useful as a hypolipidemic and hypocholesterolemic agent. A compound of Formula Ia also may be used in the preparation of atorvastatin.

The following examples are illustrated to show the present process, the preparation of starting materials, and the use of methyl (S)-3,4-O-isopropylidine- 3,4-dihydroxybutanoate, a compound of Formula I, obtained by the present process to prepare (S)-3-hydroxybutyrolactone, which is used to prepare (R)-4-bromo-3-hydroxybutyrate, which is used to prepare ethyl (R)-4-cyano-3-hydroxybutanoate, which in turn is used to prepare (5R)-1, 1-dimethylethyl 6-cyano-5-hydroxy-3-oxo-hexanoate, which in turn is used to prepare (4R-Cis)-1,1-dimethylethyl 6-cyanomethyl-2,2-dimethyl-1,3-dioxane-4-acetate, which in turn is used to prepare (4R-Cis)-1,1-dimethylethyl 6-(2-aminoethyl)-2,2-dimethyl-1,3-dioxane-4-acetate, which in turn is used to prepare (2R-trans)-5-(4-fluorophenyl)-2-(1-methylethyl)-N,4-diphenyl-1-[2-(tetrahydro-4-hydroxy-6-oxo-2H-pyran-2-yl)ethyl-1H-pyrrole-3-carboxamide or the salt of the hydroxy acid [R-(R*,R*)]-2-(4-fluorophenyl-β,δ-dihydroxy-5-(1-methylethyl)-3-phenyl-4-[(phenylamino)carbonyl]-1H-pyrrole-1-heptanoic acid calcium salt (2:1), corresponding to the opened lactone ring of the aforementioned compound, atorvastatin, useful as a hypolipidemic and hypocholesterolemic agent.

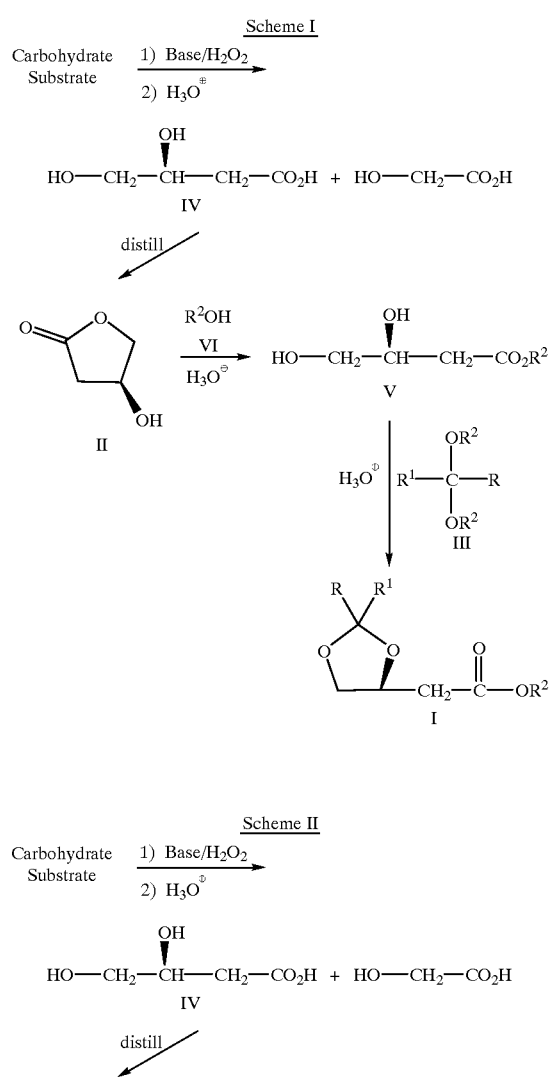

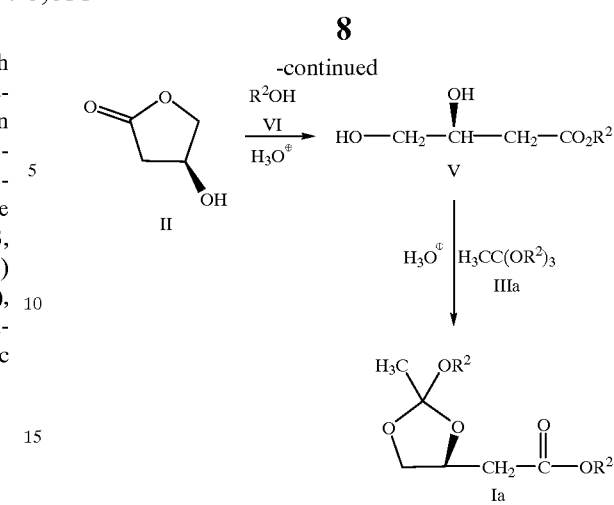

EXAMPLE 1

Methyl (S)-3,4-O-Isoprolylidene-3,4-dihydroxybutanoate

To a 1 L round bottom flask equipped with mechanical stirrer, thermocouple and reflux condenser was charged 250 g (694 mmol) lactose monohydrate, 250 mL of water and the mixture heated to 65° C. to 75° C. once the slurry was at temperature, 200 mL of sodium hydroxide solution (122 g, 1.53 mol of 50% sodium hydroxide diluted to volume) and 200 mL of hydrogen peroxide ($H_2O_2$) (35%, 75.0 g, 772 mmol diluted to volume) were added simultaneously via peristaltic pumps over a period of 7 to 10 hours. The temperature of the exothermic reaction was maintained between 65° C. to 80° C. throughout the addition. Once addition was complete, the temperature was maintained at the reaction temperature for 1 hour, then allowed to slowly cool to room temperature. Upon a negative peroxide test, the mixture was acidified to a pH of <1.5 with 37% hydrochloric acid (HCl) solution (128 mL, 1.54 mol). The water was removed by distillation at laboratory vacuum at a batch temperature of up to 65° C. The sodium chloride saturated oil was cooled slightly, 200 mL of methanol (MeOH) charged, the mixture heated to reflux, and then filtered through a fritted funnel. The salt cake was washed with an additional 2×50 mL of MeOH. HCl (anhydrous, 3.6 g) was charged to the combined methanol filtrates and the mixture heated at reflux for 2 hours. The solvent was removed by distillation at atmospheric pressure. Then a short path distillation column was attached and the mixture distilled under vacuum at a temperature of less than 75° C. until no further methyl glycolate distilled. An additional 150 mL MeOH and 3.5 g of HCl were charged, heated at reflux for 1 to 2 hours, then the remaining glycolate removed by distillation under vacuum. The contents were cooled to 50° C. to 55° C. and 5.0 g of para-toluenesulfonic acid and 50 mL of MeOH were charged. The reaction mixture was heated at 60° C. to 65° C. while dimethoxypropane (400 mL) was charged via an addition funnel over 1 to 2 hours, then held at 60° C. to 65° C. for an additional hour. Once reaction was complete, the solvent was removed at atmospheric pressure and retained for recycle. A short path distillation column was attached and the fraction that distilled at 63° C. to 90° C. (vapor temperature) at 3.4 mm Hg was retained as the crude methyl (S)-3,4-O-isopropylidene-3,4-dihydroxybutanoate in a yield of 59.7 g, (44.5%) 89.9% pure by vapor phase chromatography (VPC). This material was sufficiently pure to use as a starting material in the preparation of ethyl (R)-4-cyano-3-hydroxybutanoate, an important intermediate in the synthesis of atorvastatin (Nanninga, et al., *Tetrahedron Lett.*, 1992;33:2279). Material of higher purity may be obtained by fractional distillation if desired.

Proton nuclear magnetic resonance spectroscopy ($^1$H NMR) (200 MHz, CDCl$_3$): δ 4.43 (m, 1H), 4.10 (dd, J=8.4, 6.0 Hz, 1H), 3.64 (s, 3H), 3.60 (m, 1H), 2.66 (dd, J=15.8, 6.0 Hz, 1H), 2.46 (dd, J=15.8, 7.0 Hz, 1H), 1.35 (s, 3H), 1.30 (s, 3H). Carbon NMR ($^{13}$C NMR) (50 MHz, CDCl$_3$): δ 170.9, 109.2, 72.0, 69.1, 51.6, 38.8, 26.8, 25.5.

EXAMPLE 2

(S)-3-Hydroxybutyrolactone

To a 250 mL flask equipped with a magnetic stir bar was charged 10.0 g of the acetonide from Example 1 (95.1% pure by VPC analysis), 50.0 mL tetrahydrofuran (THF), and 10 mL 1.0 M HCl. The contents were stirred at room temperature for 6 hours until VPC analysis indicated consumption of starting material. The contents of the flask were distilled to remove all solvents at laboratory vacuum at a temperature of 50° C. to 55° C. to provide 5.80 g of dark amber oil, 95.7% pure by VPC, 99.5% yield.

$^1$H NMR (200 MHz, CDCl$_3$): δ 4.63 (m, 1H), 4.40 (dd, J=10.2, 4.3 Hz, 1H), 4.26 (dd, J=10.2, 1.2 Hz, 1H), 3.56 (bs, 1H), 2.73 (dd, J=18.0, 5.9 Hz, 1H), 2.47 (dd J=18.0, 1.2 Hz, 1H). $^{13}$C NMR (50 MHz, CDCl$_3$): δ 176.9, 76.2, 67.3, 37.7.

EXAMPLE 3

Ethyl (R)-4-Bromo-3-hydroxybutanoate

To a 50 mL round bottom flask equipped with a magnetic stirring bar and nitrogen (N$_2$) inlet was charged 2.13 g (S)-3-hydroxybutyrolactone (Example 2) (95.7% pure by VPC) and 5.0 mL acetic acid. The flask was cooled using an ice bath and 9.0 mL of 33% hydrogen bromide (HBr) in acetic acid was charged dropwise over several minutes upon which the ice bath was removed and the mixture allowed to warm to room temperature and stirred overnight under N$_2$. An additional 1.0 mL of 33% HBr in acetic acid was added when VPC indicated that the reaction was not complete, and the mixture was stirred overnight at room temperature. The reaction was quenched by pouring into ethyl alcohol (85 mL) and heated at reflux until the reaction was complete (8 hours). The solvent was removed and the residue taken up in ethyl acetate (100 mL), washed with dilute aqueous sodium bicarbonate (NaHCO$_3$) solution (25 mL), water (25 mL), and brine (25 mL). The organic layer was distilled and the residue purified by silica gel chromatography to yield 1.74 g (41.5%) of the title compound.

$^1$H NMR (200 MHz, CDCl$_3$): δ 4.20 (m, 1H), 4.18 (t, J=7.1 Hz, 2H), 3.48 (m, 2H), 3.34 (d, J=5.0 Hz, 1H), 2.65 (m, 2H), 1.28 (t, J=7.1 Hz, 3H).

$^{13}$C NMR (50 MHz, CDCl$_3$): δ 171.5, 67.6, 60.9, 39.4, 37.2, 14.0.

EXAMPLE 4

(5R)-1,1-Dimethylethyl 6-cyano-5-hydroxy-3-oxo-hexanoate

Step A: Preparation of (R)-4-cyano-3-hydroxybutyric acid, ethyl ester

To a 50 gallon reactor containing a solution of 2.2 kg (44 mol) of sodium cyanide dissolved in 40 L of demineralized water was added 7 kg (33 mol) of (S)-4-bromo-3-hydroxybutyric acid, ethyl ester (Example 3) dissolved in 8 L of ethanol. The reaction mixture was stirred for 16 hours at room temperature. Ethyl acetate (65 L) was added, the mixture agitated, and the layers were allowed to separate. The lower aqueous layer was transferred to a 50 gallon vessel containing 2.5 kg of sodium chloride and 65 L of ethyl acetate, the mixture was agitated and the layers allowed to separate, and the lower aqueous layer was cut off. The organic layers were combined and concentrated in vacuo. The residue was distilled to afford 3.1 kg of the title compound; bp 110–125° C. 0.5 mm Hg; optical rotation $[\alpha]_D^{25}$=33.1° (C=1.08, chloroform);

VPC: 30 meter DB-5 capillary column 100 (2) to 280 (15) at 15° C./minute, 7.28 minutes retention time, 95.6% area.

$^1$H NMR (200 MHz, CDCl$_3$): δ 4.36 (q, 1H), 4.18 (q, 2H), 3.84 (bs, 1H), 2.64 (m, 4H), 1.29 (t, 3H).

Step B: Preparation of (5R)-1,1-Dimethylethyl 6-cyano-5-hydroxy 3-oxo-hexanoate

To a stirred –50° C. solution of lithium diisopropylamide (100 kg of 2 M) in tetrahydrofuranheptane was added tertiary-butyl acetate (30 kg, 255 mol) followed by a rinse of 3 kg of tetrahydrofuran, and the mixture was stirred to –45° C. to –5° C. for 50 minutes. (R)-4-cyano-3-hydroxybutyric acid, ethyl ester (Step A) (10 kg, 64 mol) as a solution in 30 kg of tetrahydrofuran was then added to the previous mixture. The reaction mixture was stirred for 30 minutes at –5° C. to –30° C., and transferred to 240 L of 0° C. 2.8N aqueous hydrochloric acid solution. The aqueous layer was extracted with 50 kg of ethyl acetate, the aqueous layer was separated and reextracted with 36 kg of ethyl acetate, the extracts are combined, and concentrated in vacuo to afford crude (5R)-1,1-dimethylethyl 6-cyano-5-hydroxy-3-oxo-hexanoate which was not isolated. A small sample was purified by column chromatography on flash silica gel eluting with 1:1 hexane:ethyl acetate.

$^1$H NMR (200 MHz, CDCl$_3$): 4.40 (m, 1H), 3.58 (bs, 1H), 3.43 (s, 2H), 2.88 (d, 2H), 2.61 (m, 2H), 1.48 (s, 9H). Mass spectrum (MS) (EI) m/e, (%): 229 (3), 228 (26), 173 (10), 172 (100), 154 (62), 112 (30), 59 (50), 57 (77).

EXAMPLE 5

(4R-Cis)-1-1-Dimethylethyl 6-cyanomethyl-2,2-dimethyl-1,3-dioxane-4-acetate Step A: Preparation of [R-(R*,R*)]-1,1-Dimethylethyl 6-cyano-3,5-dihydroxyhexanoate Crude (5R)-1,1-dimethylethyl 6-cyano-5-hydroxy-3-oxo-hexanoate (Example 4), approximately 52 mol, was dissolved in 90 L of tetrahydrofuran and 19 L of methanol under a nitrogen atmosphere. This solution was cooled to –85° C. and 24 L of a 50% solution of methoxy-diethylborane in tetrahydrofuran was added. The reaction was cooled to –97° C. and 3.6 kg (126 mol) of sodium borohydride was added in 0.2 kg portions over 3 hours. The reaction was maintained between –93° C. and –85° C. for 5 hours and allowed to warm to room temperature and stand for 10 hours under a nitrogen atmosphere. The reaction was quenched by the addition of 7.5 L (118.5 mol) acetic acid and concentrated by vacuum distillation to an oil. The residue was dissolved with 40 L of methanol, concentrated by vacuum distillation, redissolved with 44 L of methanol, and reconcentrated by vacuum distillation to give a brown oil. This oil was taken up in 90 L of ethyl acetate and washed with 30 L of deionized water. The ethyl acetate solution was concentrated by vacuum distillation to give the title compound, [R-(R*,R*)]-1,1-dimethylethyl 6-cyano-3,5-dihydroxyhexanoate, which was used without further purification.

Step B: Preparation of (4R-Cis)-1,1-dimethylethyl 6-cyanomethyl-2,2-dimethyl-1,3-dioxane-4-acetate Crude [R-(R*,R*)]-1,1-dimethylethyl 6-cyano-3,5-dihydroxyhexanoate (Step A) (approximately 50 mol) was dissolved in 67.5 L of 2,2-dimethoxypropane and 38.0 L of acetone. Methanesulfonic acid (167 mL) was added, and the solution stirred for 2 hours at room temperature. After the addition of 50 L of aqueous sodium bicarbonate and 80 L of ethyl acetate, the reaction was agitated, the layers separated, and the organic layer diluted with 80 L of hexane. The organic layer was washed two times with 100 L of water. After concentration by vacuum distillation, the residue was dissolved in 80 L of warm hexane. Crystals formed upon cooling to provide 10.1 kg of product as an off-white solid after collection by filtration and drying. This material was recrystallized by dissolving in 80 L of heptane by warming to 50° C., cooling slowly to 10° C., and collecting the product by filtration. After drying, 9.1 kg of (4R-cis)-1,1-dimethyl 6-cyanomethyl-2,2-dimethyl-1,3-dioxane-4-acetate was obtained as an off-white solid; mp 64.7–68° C.

$^1$H NMR (200 MHz, CDCl$_3$): δ 4.32 (m, 1H), 4.18 (m, 1H), 2.55 (d, 2H, J=6.1 Hz), 2.5–2.7 (m, 1H), 2.40 (dd, J=6.2 Hz, 15.4 Hz, 1H), 1.79 (dt, J=2.5 Hz, 12.1 Hz, 1H), 1.50 (s, 3H), 1.49 (s, 9H), 1.42 (s, 3H), 1.36 (m, 1H).

$^{13}$C NMR (50 MHz, CDCl$_3$): δ 19.74, 25.09, 28.24, 29.88, 35.58, 42.50, 65.20, 65.81, 80.87, 99.48, 116.68, 169.75.

Gas Chromatography/Mass Spectrometry (GC/MS) m/e: 254, 198, 154, 138, 120, 59, 57, 43, 41.

Fourier Transform Infrared Spectroscopy (FTIR) (KBr): 941.4, 1116.2, 1154.8, 1188.3, 1257.7, 1293.7, 1309.1, 1368.3, 1725.8, 2361.1, 2983.5, 2996.4 cm$^{-1}$.

EXAMPLE 6

(4R-Cis)-1,1-dimethylethyl 6-(2-aminoethyl)-2,2-dimethyl 1,3 dioxane-4-acetate

A solution of (4R-cis)-1,1-dimethylethyl 6-cyanomethyl-2,2-dimethyl-1,3-dioxane-4-acetate (Example 5), 8.2 kg (30.5 mol) in 100 L of methanol containing 15 kg of anhydrous ammonia was reacted with hydrogen gas under 50 pounds per square inch (psi) at 30° C. in the presence of a slurry of 8 kg of Raney nickel doped with 1% molybdenum. After 6 hours, uptake of hydrogen had ceased, the mixture was cooled to 20° C., the atmosphere was vented and exchanged for nitrogen, and the slurry was filtered, concentrated by distillation and distilled under vacuum to give 7.8 kg of 96% pure (4R-cis)-1,1-dimethylethyl 6-(2-aminoethyl)-2,2-dimethyl-1,3-dioxane-4-acetate as a clear oil; bp 125–135° C. at 0.5 mm Hg.

1H NMR (200 MHz, CDCl$_3$): 4.12 (m, 1H), 3.82 (m, 1H), 2.66 (t, J=6.6 Hz, 2H), 2.29 (dd, J=15.1 Hz, 7.0 Hz, 1H), 2.15 (dd, J=15.1 Hz, 6.2 Hz 1H), 1.35–1.45 (m, 3H), 1.31 (s, 12H), 1.22 (s, 3H), 1.0–1.2 (m, 1H).

$^{13}$C NMR (50 MHz, CDCl$_3$): 5 169.8, 98.4, 80.2, 67.2, 66.1, 42.6, 39.8, 38.3, 36.5, 30.0, 28.0, 19.6. GC/MS m/e: 202, 200, 173, 158, 142, 140, 114, 113, 100, 99, 97, 72, 57.

FTIR (neat): 951.6, 1159.9, 1201.1, 1260.3, 1314.3, 1368.3, 1381.2, 1731.0, 2870.3, 2929.8, 2980.9, 3382.2 cm$^{-1}$.

EXAMPLE 7

(±)4-Fluoro-α-[2-methyl-1-oxopropyl]-γ-oxo-N,β-diphenylbenzenebutaneamide mixture of [R-(R*, R)], [R-(R*.S*)], [S-(R*,R*)] and [S-(R*,S*)] isomers Step A: Preparation of 4-Methyl-3-oxo-N-phenyl-2-(phenylmethylene)pentanamide A suspension of 100 kg of 4-methyl-3-oxo-N-phenyl-pentanamide (Example A) in 660 kg of hexane was treated with agitation under nitrogen with 8 kg of β-alanine, 47 kg of benzaldehyde, and 13 kg of glacial acetic acid. The resulting suspension was heated to reflux with removal of water for 20 hours. An additional 396 kg of hexane and 3 kg of glacial acetic acid was added and reflux continued with water removal for 1 hour. The reaction mixture was cooled to 20° C. to 25° C., and the product was isolated by filtration. The product was purified by slurring in hexane at 50° C. to 60° C., cooling, and filtrating. The product was slurred twice with water at 20° C. to 25° C., filtered, and dried in vacuo to yield 110 kg of 4-methyl-3-oxo-N-phenyl-2-(phenylmethylene)pentanamide, mp 143.7–154.4° C. VPC: 30 meter DB-5 capillary column 50° C. to 270° C. at 15° C./min; 19.33 minutes, 99.7% (area). GC/MS: M/Z 293 [M]$^+$.

$^1$H NMR (200 MHz, CDCl$_3$): δ 8.01 (bs, 1H), 7.49 (m, 5H), 7.28 (m, 5H), 7.09 (m, 1H), 3.30 (quint, 1H), 1.16 (d, 6H).

Step B: Preparation of (±) 4-Fluoro-α-[2-methyl-1-oxopropyl]γ-oxo-N-β-diphenylbenzenebutaneamide mixture of [R-(R*,R*)], [R-(R*,S*)], S-(R*,R*)] and [S(R*,S*) lisomers A solution of 17.5 kg of 3-ethyl-5-(2-hydroxyethyl)-4-methylthiazolium bromide in 300 L of anhydrous ethanol was concentrated by distillation of 275 L of the ethanol. Under an argon atmosphere, 100 kg (340 mol) of 4-methyl-3-oxo-N-phenyl-2-(phenylmethylene)pentanamide (Step A), 47.5 L (340 mol) of triethylamine, and 40 L (375 mol) of 4-fluorobenzaldehyde were added. The resulting solution was stirred and heated at 75° C. to 80° C. for 23 hours. The slurry was dissolved in 600 L of isopropanol at 80° C. The resulting solution was slowly cooled, and the product isolated by filtration. Washing the precipitate with isopropanol and drying in vacuo afforded 99 kg of (±) 4-fluoro-α-[2-methyl-1-oxopropyl]-γ-oxo-N-β-diphenylbenzenebutaneamide as a mixture of [R-(R*,R*)], [R-(R*,S*)], [S-(R*,R*)] and [S-(R*,S*)] isomers; mp 206.8–207.6° C.

$^1$H NMR (200 MHz, CDCl$_3$): δ 9.41 (bs, 1H), 8.17 (dd, 2H), 6.98–7.43 (m, 12H), 5.51 (d, J=11 Hz, 1H), 4.91 (d, J=11 Hz, 1H), 2.98 (quin., 1H), 1.22 (d, 3H), 1.03 (d, 3H).

High Pressure Liquid Chromatography (HPLC): (Acetonitrile:tetrahydrofuran:water) (40:25:55) Econosil C$_{18}$, 5μ, 25 cm, 1.0 mL/min, 254 nm, 16.77 minutes, 99.2% (area).

EXAMPLE 8

[R-(R*,R*)]-2-(4-Fluorophenyl)-β, δ-dihydroxy-5-(1-methylethyl)-3-phenyl-4[phenylaminocarbonyl]-1H-pyrrole-1-heptanoic acid, calcium salt (2:1)

A solution of (4R-cis)-1,1-dimethylethyl 6-(2-aminoethyl)-2,2-dimethyl-1,3-dioxane-4-acetate, 7.8 kg (Example 6), (±)4-fluoro-α-[2-methyl-1-oxopropyl]-γ-oxo-N-β-diphenyl-benzenebutaneamide mixture of [R-(R*,R*)], [R-(R*,S*)], [S-R*,R*)] and [S-(R*,S*)]isomers, 12.8 kg (Example 7), and 2.1 kg of pivalic acid in 120 L heptane/30

L THF were heated at reflux for 40 hours. The solution was cooled, diluted with 90 L tert-butyl methyl ether and 5.0 L methanol then washed with dilute sodium hydroxide (61.6 L), dilute HCl (62.6 L), then the solvent removed by distillation. The product oil was taken up in methanol (75.0 L) and 1.6 kg 37% HCl in 15 L water was charged and the reaction mixture stirred at room temperature for 12 hours. A solution of 4.0 kg of 50% sodium hydroxide in 20 L of water was charged and stirred at room temperature for 2 hours. The reaction mixture was diluted with water (112 L) and washed with tert-butyl methyl ether (400 L). The aqueous layer containing the product was acidified with HCl (3.8 kg 37%) in 10 L water and taken up in tert-butyl methyl ether (200 L). The product acid was diluted with methanol (66.0 L) and saponified with 1.8 kg of 50% sodium hydroxide in 134 L of water for 30 minutes. The aqueous product layer was isolated and heated at reflux for 16 hours. The solution was cooled then washed with tert-butyl methyl ether (167.5 L). The product salt was diluted with water (134 L) and 2.50 kg of calcium acetate in 66 L water was added and the reaction mixture stirred at room temperature for 1.2 hours as the product precipitated. The calcium salt was taken up in ethyl acetate/heptane (128 L/70 L) at 50° C., and the aqueous phase extracted again with ethyl acetate/heptane (60.0 L/42.0 L) at 50° C. The combined organic extracts were washed with an aqueous calcium acetate/methanol solution (0.63 kg calcium acetate in 165 L water/methanol 10:1), and the product precipitated from the hot (50° C.) organic solvents. The product salt cake was washed with heptane/ethyl acetate and then dried under vacuum to yield 10.1 kg (57.4%) of white solid.

$^1$H NMR (200 MHz, DMSO-$d_6$): δ 9.82 (s, 1H), 7.52 (d, 2H), 7.22 (m, 6H), 7.08 (m, 4H), 7.00 (m, 2H), 5.75 (s, 1H), 4.80 (s, 1H), 3.96 (m, 1H), 3.79 (m, 2H), 3.54 (m, 1H), 3.24 (m, 1H), 2.11 (m, 2H), 1.98 (m, 2H), 1.59 (m, 2H), 1.26–1.37 (m, 8H).

$^{13}$C NMR (50 MHz, DMSO-$d_6$): δ 178.4, 166.2, 163.2, 160.0, 139.4, 136.0, 134.9, 133.4, 133.3, 129.1, 128.7, 128.4, 127.6, 127.3, 125.3, 123.0, 120.6, 119.4, 117.5, 115.5, 115.2, 66.3, 43.9, 43.6, 40.9, 39.1, 25.6, 22.3.

PREPARATION OF STARTING MATERIALS

EXAMPLE A

4-Methyl-3-oxo-N-phenylpentanamide

A three-necked, 12 L round bottom flask equipped with a mechanical stirrer, a thermometer, and set up for distillation was charged with 2.6 L of toluene, 1.73 kg (12 mol) of methyl 4-methyl-3-oxopentanoate and 72 g (1.18 mol) of ethylenediamine. The mixture was heated to 80° C. and charged with 0.49 kg of aniline. The mixture was brought to reflux and distillation was started. After 40 minutes, a further 0.245 kg of aniline was charged and, at 40 minute intervals, a further two portions of aniline (0.245 and 0.25 kg) were charged. Distillation was continued for a further 1 to 5 hours until a total of 985 mL of solvent was removed. The solution was stirred at room temperature for 16 hours, and a further 550 mL of solvent was removed by vacuum distillation (at approximately 85 mm Hg). The mixture was cooled, and 2 L of water was charged to provide an oil. The mixture was warmed to 40° C., and a further 1.0 L of water was charged. Seven hundred milliliters of toluene/water mixture was removed by vacuum distillation (approximately 20 mm Hg). Two liters of water were charged, and the mixture allowed to stand for 10 days. The product was isolated by filtration and washed with three portions of hexane. Drying in vacuo gave 1.7 kg of 4-methyl-3-oxo-N-phenylpentanamide as a hydrate; mp 46.5–58.8° C.

HPLC: 98.8%—retention time 3.56 minutes, acetonitrile/water 65:35 on a dry basis.

VPC: 87.6%—retention time 12.43 minutes, also 10.8% aniline (decomposition).

We claim:

1. A process for the preparation of a compound of Formula I

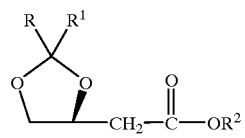

wherein R and R$^1$ are each independently alkyl of from 1 to 3 carbon atoms; and R$^2$ is alkyl of from 1 to 8 carbon atoms, which comprises:

Step (a) treating a carbohydrate substrate in a solvent with hydrogen peroxide in the presence of a base and subsequent acidification with an acid to afford a mixture comprising a compound of Formula IV

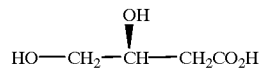

and glycolic acid;

Step (b) removing the solvent to convert the compound of Formula IV to the compound of Formula II

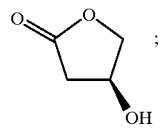

Step (c) treating the mixture containing the compound of Formula II with an alcohol of Formula VI

wherein R$^2$ is as defined above in the presence of an acid catalyst to afford a compound of Formula V

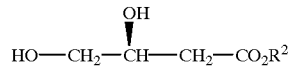

wherein R$^2$ is as defined above; and

Step (d) treating the mixture containing a compound of Formula V with a compound of Formula III

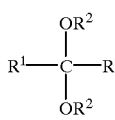

III wherein R, $R^1$, and $R^2$ are as defined above in the presence of an acid catalyst to afford a compound of Formula I.

2. The process according to claim 1 wherein the carbohydrate substrate in Step (a) is selected from the group consisting of: a water soluble carbohydrate, a disaccharide; and a water soluble carbohydrate, a higher oligomer.

3. The process according to claim 2 wherein the carbohydrate substrate is selected from the group consisting of: lactose; maltose; and maltodextrins.

4. The process according to claim 3 wherein the carbohydrate substrate is lactose.

5. The process according to claim 1 wherein the base in Step (a) is selected from the group consisting of: an alkali metal hydroxide; and an alkaline earth metal hydroxide.

6. The process according to claim 5 wherein the base is sodium hydroxide.

7. The process according to claim 1 wherein the acid in Step (a) is selected from the group consisting of: hydrochloric acid; and hydrobromic acid.

8. The process according to claim 7 wherein the acid is hydrochloric acid.

9. The process according to claim 1 wherein the solvent in Step (a) is water.

10. The eprocess according to claim 1 wherein in Step (b) the solvent is removed under vacuum at a temperature of about 35° C. to about 75° C.

11. The process according to claim 1 wherein in Step (c) the alcohol of Formula VI is selected from the group consisting of: methanol; and ethanol.

12. The process according to claim 11 wherein the alcohol is methanol.

13. The process according to claim 1 wherein in Step (c) the acid catalyst is selected from the group consisting of: hydrochloric acid; sulfuric acid; and para-toluenesulfonic acid.

14. The process according to claim 13 wherein the acid catalyst is hydrochloric acid.

15. The process according to claim 1 wherein in Step (d) the compound of Formula III is selected from the group consisting of: dimethoxypropane; and diethoxypropane.

16. The process according to claim 15 wherein the compound of Formula III is dimethoxypropane.

17. The process according to claim 1 wherein the acid catalyst in Step (d) is selected from the group consisting of: a mineral acid; and an organic acid.

18. The process according to claim 17 wherein the acid catalyst is selected from the group consisting of: hydrochloric acid; and para-toluenesulfonic acid.

19. The process according to claim 18 wherein the acid catalyst is para-toluenesulfonic acid.

20. The process according to claim 1 for the preparation of methyl (S)-3,4-O-isopropylidene-3,4-dihydroxybutanoate.

21. A process for the preparation of a compound of Formula Ia

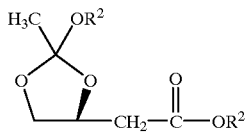

Ia wherein $R^2$ is alkyl of from 1 to 8 carbon atoms, which comprises:

Step (a) treating a carbohydrate substrate in a solvent with hydrogen peroxide in the presence of a base and subsequent acidification with an acid to afford a mixture comprising the compound of Formula IV

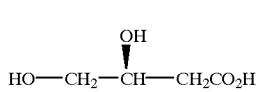

IV and glycolic acid;

Step (b) removing the solvent to convert the compound of Formula IV to the compound of Formula II

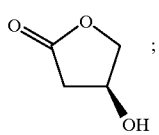

II

Step (c) treating the mixture containing the compound of Formula II with an alcohol of Formula VI

$R^2$—OH    VI wherein $R^2$ is as defined above in the presence of an acid catalyst to afford a compound of Formula V

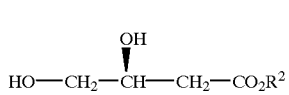

V wherein $R^2$ is as defined above; and

Step (d) treating the mixture containing a compound of Formula V with a compound of Formula IIIa

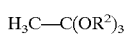

$H_3C$—$C(OR^2)_3$    IIIa wherein $R^2$ is as defined above in the presence of an acid catalyst to afford a compound of Formula Ia.

22. The process according to claim 21 wherein the carbohydrate substrate in Step (a) is selected from the group consisting of: a water soluble carbohydrate, a disaccharide; and a water soluble carbohydrate, a higher oligomer.

23. The process according to claim 22 wherein the carbohydrate substrate is selected from the group consisting of: lactose; maltose; and maltodextrins.

24. The process according to claim 23 wherein the carbohydrate substrate is lactose.

25. The process according to claim 21 wherein the base in Step (a) is selected from the group consisting of: an alkali metal hydroxide; and an alkaline earth metal hydroxide.

26. The process according to claim 25 wherein the base is sodium hydroxide.

27. The process according to claim 21 wherein the acid in Step (a) is selected from the group consisting of: hydrochloric acid; and hydrobromic acid.

28. The process according to claim 27 wherein the acid is hydrochloric acid.

29. The process according to claim 21 wherein the solvent in Step (a) is water.

30. The process according to claim 21 wherein in Step (b) the solvent is removed under vacuum at a temperature of about 35° C. to about 75° C.

31. The process according to claim 21 wherein in Step (c) the alcohol of Formula VI is selected from the group consisting of: methanol; and ethanol.

32. The process according to claim 31 wherein the alcohol is methanol.

33. The process according to claim 21 wherein in Step (c) the acid catalyst is selected from the group consisting of: hydrochloric acid; sulfuric acid; and para-toluenesulfonic acid.

34. The process according to claim 33 wherein the acid catalyst is hydrochloric acid.

35. The process according to claim 21 wherein in Step (d) the compound of Formula IIIa is selected from the group consisting of: trimethyl orthoacetate; and triethyl orthoacetate.

36. The process according to claim 35 wherein the compound of Formula IIIa is trimethyl orthoacetate.

37. The process according to claim 21 wherein the acid catalyst in Step (d) is selected from the group consisting of: a mineral acid; and an organic acid.

38. The process according to claim 37 wherein the acid catalyst is selected from the group consisting of: hydrochloric acid; and para-toluenesulfonic acid.

39. The process according to claim 38 wherein the acid catalyst is para-toluenesulfonic acid.

* * * * *